United States Patent [19]

Jennings

[11] Patent Number: 5,204,478
[45] Date of Patent: Apr. 20, 1993

[54] PROCESS FOR THE SYNTHESIS OF 2,6-DICHLORO-5-FLUORONICOTINIC ACID AND 2,6-DICHLORO-5-FLUORONICOTINOYL CHLORIDE

[75] Inventor: Rex A. Jennings, Holland, Mich.

[73] Assignee: Warner-Lambert Company, Morris Plains, N.J.

[21] Appl. No.: 932,452

[22] Filed: Aug. 20, 1992

[51] Int. Cl.⁵ .......................................... C07D 213/55
[52] U.S. Cl. .................................... 546/315; 546/318
[58] Field of Search ................................ 546/315, 318

[56] References Cited

FOREIGN PATENT DOCUMENTS 0333020 9/1989 European Pat. Off. .

Primary Examiner—Marianne M. Cintins
Assistant Examiner—Michael B. Hydorn
Attorney, Agent, or Firm—Francis J. Tinney

[57] ABSTRACT

An improved process for the preparation of 2,6-dichloro-5-fluoronicotinoyl chloride is described where a 2,6-dihydroxy-5-fluoronicotinic acid ester is converted in one step using phosphorus oxychloride and a lithium reagent to 2,6-dichloro-5-fluoronicotinoyl chloride and subsequent basic hydrolysis affords 2,6-dichloro-5-fluoronicotinic acid.

27 Claims, No Drawings

PROCESS FOR THE SYNTHESIS OF 2,6-DICHLORO-5-FLUORONICOTINIC ACID AND 2,6-DICHLORO-5-FLUORONICOTINOYL CHLORIDE

BACKGROUND OF THE INVENTION

Substituted pyridines are of interest as intermediates in the synthesis of naphthyridine antibacterial agents. 2,6-Dichloro-5-fluoronicotinic acid and 2,6-dichloro-5-fluoronicotinoyl chloride are of particular interest as key intermediates in the synthesis of naphthyridine antibacterial agents as disclosed in European Published Patent Applications 0132,845, 0160,578, 0153,580 and U.S. Pat. Nos. 4,840,954, 4,649,144, and 4,616,019.

A process for preparing 2,6-dichloro-5-fluoronicotinic acid is disclosed in European Published Patent Application 0333,020. However, this process suffers from several major disadvantages. In our hands the conversion of 2,6-dihydroxy-3-cyano-5-fluoropyridine to 2,6-dichloro-3-cyano-5-fluoropyridine using phosphorus oxychloride and phosphorus pentachloride produces 2,4,6-trichloro-3-cyano-5-fluoropyridine as a byproduct. This results a lower yield of the desired 2,6-dichloro-3-cyano-5-fluoropyridine and especially after the hydrolysis the products of this trichloronitrile contaminate the desired nicotinic acid product. As a result, additional purification procedures are required to remove the trichloronitrile byproduct. Finally, another major drawback is the mediocre overall yield (40%–45%) in converting 2,6-dihydroxy-3-cyano-5-fluoropyridine to 2,6-dichloro-5-fluoronicotinic acid. This may be an inherent problem in hydrolyzing the 2,6-dichloro-3-cyano-5-fluoropryridine. E. P. Oliveto states "the hydrolysis of chlorocyanopyridine to chloropyridine acids cannot be considered a generally useful reaction because 2 and 4 halogens are easily hydrolyzed" (see *The Chemistry of Heterocyclic Compounds, Pyridine and its Derivatives*. Part III. Weissberger, A (Ed.) Interscience Publishers, New York, N.Y. 1962:244).

Thus, we have surprisingly and unexpectedly found that a 2,6-dihydroxy-5-fluoronicotinate can be converted with phosphorus oxychloride in the presence of a lithium reagent to 2,6-dichloro-5-fluoronicotinoyl chloride which is subsequently converted to 2,6-dichloro-5-fluoronicotinic acid.

The object of the present invention is an improved process for preparing 2,6-dichloro-5-fluoronicotinic acid and 2,6-dichloro-5-fluoronicotinoyl chloride by using a novel synthetic scheme.

The present method utilizes inexpensive starting materials, proceeds in fewer steps, and affords higher yields compared to the previous methods. In addition, the present process obviates the need for phosphorus pentachloride with its concomitant overchlorination tendencies (see Mosher HS in Elderfield's *Heterocyclic Compounds*, John Wiley and Sons, Inc., New York, N.Y., 1950;1:514) and eliminates the need for carrying out a hydrolysis reaction under drastic conditions on a substrate with sensitive functionality.

SUMMARY OF THE INVENTION

Accordingly, a first aspect of the present invention is an improved process for the preparation of the compound of Formula I

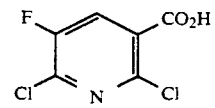

which comprises:
Step (a) heating a compound of Formula III

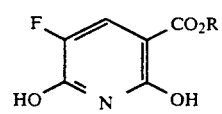

wherein R is lower alkyl or benzyl with POCl$_3$ in the presence of a lithium reagent and subsequently diluting with a solvent, filtering and distilling to afford the compound of Formula II; and

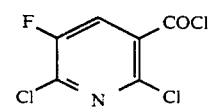

Step (b) reacting the compound of Formula II in water with a base, extracting the resulting solution with a solvent, and neutralized with an acid to afford the compound of Formula I.

A second aspect of the present invention is an improved process for the preparation of the compound of Formula II

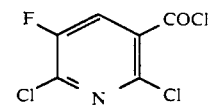

which comprises heating a compound of Formula III

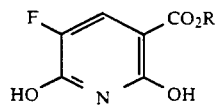

wherein R is lower alkyl or benzyl with POCl$_3$ in the presence of a lithium reagent and subsequently diluting with a solvent, filtering and distilling to afford the compound of Formula II.

DETAILED DESCRIPTION OF THE INVENTION

In this invention the term "alkyl" means a straight or branched hydrocarbon radical having from one to six carbon atoms and includes, for example, methyl, ethyl, n-propyl, isopropyl, n-butyl, secondary butyl, isobutyl, tertiary butyl, n-pentyl, n-hexyl, and the like.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, magnesium, and the like.

The process of the present invention is a new, improved, economical, and commercially feasible method for preparing 2,6-dichloro-5-fluoronicotinoyl chloride and 2,6-dichloro-5-fluoronicotinic acid. The process of the present invention is outlined in the following Scheme I:

SCHEME 1

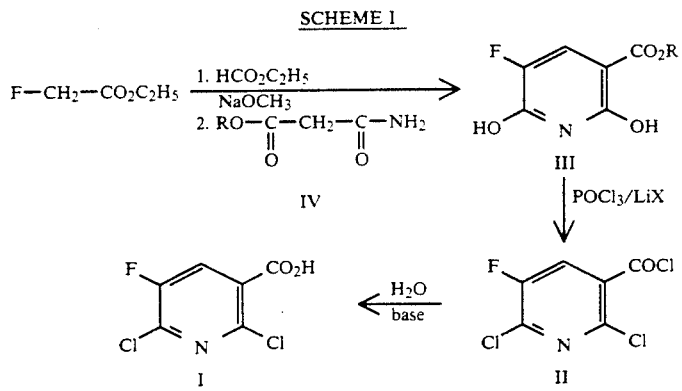

A compound of Formula III wherein R is lower alkyl or benzyl is prepared by treating ethyl fluoroacetate with ethyl formate in the presence of a base such as, for example, sodium methoxide, and the like at about 0° C. and subsequently a solution of a compound of Formula IV wherein R is as defined above is added to the previous mixture in a solvent, such as, for example, methanol and the like and the mixture heated to about the reflux temperature of the solvent. The resulting mixture is treated with an acid such as, for example, 37% hydrochloric acid and the like to afford a compound of Formula III. Preferably, the reaction is carried out wherein R is methyl in a compound of Formula III and Formula IV, the base is sodium methoxide, the solvent is methanol, the mixture heated at reflux, and the acid is 37% hydrochloric acid solution.

The compound of Formula II is prepared by treating a compound of Formula III with excess phosphorus oxychloride in the presence of a lithium reagent such as a lithium salt (LiX, wherein X is acetate, carbonate, chloride, hydroxide, oxide, phosphate, sulfate, and the like), for example, lithium acetate, lithium carbonate, lithium chloride, lithium hydroxide monohydrate, lithium oxide, lithium phosphate, lithium sulfate, and the like by heating in a sealed system such as, for example, an autoclave and the like, at about 110° C. to about 250° C. for about 1 to about 100 hours, subsequently diluting the cooled mixture with a solvent such as, for example, a nonreactive solvent, for example, dichloromethane and the like, filtering the precipitated inorganic salts and distilling the product to afford the compound of Formula II. Preferably, the reaction is carried out with phosphorus oxychloride and lithium phosphate a about 170° C. for about 20 hours and diluting the resulting mixture with dichloromethane.

Alternatively, after the initial filtration of precipitated salts, the mother liquors can be treated with an acid chloride such as, for example, thionyl chloride which converts higher molecular weight lithium phosphates to precipitated lithium chloride and volatile phosphorus oxychloride.

The compound of Formula I is prepared by hydrolyzing the compound of Formula II with a base such as, for example, an alkali metal hydroxide, an alkali metal carbonate, an alkali metal bicarbonate, an alkaline earth metal hydroxide, alkaline earth metal carbonate, an alkaline earth metal bicarbonate, and the like, for example, sodium hydroxide, potassium hydroxide, sodium carbonate, potassium carbonate, sodium bicarbonate, potassium bicarbonate, calcium hydroxide, calcium carbonate, calcium bicarbonate, and the like in water at about pH 10 at a temperature of about 50° C. to about 60° C. and subsequently cooling the solution, extracting with a solvent such as, for example, dichloromethane and the like and neutralizing with an acid such as 37% hydrochloric acid and the like to about pH 1 to 2 to afford the compound of Formula I. Preferably, the reaction is carried out with 50% aqueous solution of sodium hydroxide at about pH 10, extracting with dichloromethane, and neutralizing with 37% aqueous hydrochloric acid solution to about pH 1 to 2.

A compound of Formula IV is either known or capable of being prepared by methods known in the art (Snyder HR, Elston CT, *Journal of the American Chemical Society* 1954;76:3039 and Paraskewas S, *Synthesis* 1974:574).

European Published Patent Applications 0,132,845, 0,160,578, and 0,153,580 and U.S. Pat. Nos. 4,840,954, 4,649,144, and 4,616,019 disclose the use of 2,6-dichloro-5-fluoronicotinic acid and 2,6-dichloro-5-fluoronicotinoyl chloride in the preparation of naphthyridine antibacterial agents.

The following examples are illustrative to show the present process and the preparation of starting materials.

EXAMPLE 1

2,6-Dichloro-5-fluoronicotinoyl chloride

To a Monel autoclave is charged methyl 2,6-dihydroxy-5-fluoronicotinate (10 g) (Example A), phosphorus oxychloride (100 mL), and lithium phosphate (6 g). The sealed autoclave is then heated at 170° C. for 20 hours. After cooling, the reaction mixture is rinsed into a round-bottom flask with methylene chloride.

The cleaned Monel autoclave is then recharged with methyl 2,6-dihydroxy-5-fluoronicotinate (15 g) (Example A), phosphorus oxychloride (150 mL), and lithium phosphate (9 g). The sealed autoclave is then heated at 170° C. for 20 hours. After cooling, the reaction mixture is slurried with methylene chloride (100 mL) and combined with the reaction mixture from the first run.

The combined mixture is filtered, the solids washed with methylene chloride, and the filtrates and washings combined and concentrated at 50°-60° C. and 30 mm Hg. The residual oil is treated with thionyl chloride (70 mL) at reflux for 3 hours. The cooled mixture is diluted with methylene chloride and filtered. The collected solid is washed with methylene chloride. After combining the filtrates and washes and then concentrating at 50°–60° C. and 30 mm Hg, the residual oil is subjected to distillation through a 3-inch Vigreaux column. The fraction with bp 71–75 @0.5 mm Hg is collected to give 2,6-Dichloro-5-fluoronicotinoyl chloride (26 g, 85%): VPC 97.2%.

EXAMPLE 2

2,6-Dichloro-5-fluoronicotinic acid

To each of two pyrex tubes is charged methyl 2,6-dihydroxy 5-fluoronicotinate (5 g) (Example A), phosphorus oxychloride (50 mL), and lithium chloride (2.5 g). The sealed tubes are heated in an oil bath at 152°–158° C. for 25 hours. After cooling, to each tube is added methylene chloride (50 mL). The reaction mixtures are combined, filtered, and the filtrates concentrated at 50° C. and 30 mm Hg. and subjected to short path vacuum distillation to a pot temperature of 160° C. to give 2,6-dichloro-5-fluoronicotinoyl chloride (10.3 g): bp 70°–100° C. @1–2 mm Hg; VPC 88.3%.

A portion of the above acid chloride (9.84 g) is slurried with 60 mL of 50°–60° C. water and then 50% aqueous sodium hydroxide is added slowly to give a homogeneous solution of pH 10. The cooled solution is extracted twice with methylene chloride, then evacuated to remove residual methylene chloride. After cooling in an ice bath. 37% hydrochloric acid is added to pH 1–2. The precipitated solid is collected, washed with water, and vacuum dried to give 2,6-dichloro-5-fluoronicotinic acid (7.5 g, 71%): mp 154.6°–154.9° C. (literature. mp 153°–155° C., Cain MH, European Published Patent Application 0333,020), HPLC 99.4%.

PREPARATION OF STARTING MATERIAL

Example A

Methyl 2,6-dihydroxy-5-fluoronicotinate

To a solution of ethyl fluoroacetate (34 g) and ethyl formate (28 g) at 0° C. is added sodium methoxide (26 g). After 3.5 hours at 20° C., a solution of methyl malonamate (40 g) in methanol (350 mL) is added and the mixture heated at reflux for 0.5 hour. To the hot mixture is added a solution of 37% hydrochloric acid (48 mL) in water (352 mL). The reaction mixture is heated at reflux for 10 minutes. After standing at 0° C. for 18 hours, the mixture is filtered and the collected solid is washed with 3 to 400 mL of water and then vacuum dried to give methyl 2,6-dihydroxy-5-fluoronicotinate, (36.6 g, 61%): mp 208°–213° C.; HPLC 95.4%.

I claim:

1. A process for the preparation of the compound of Formula I

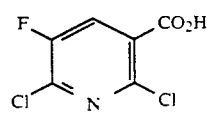

which comprises:
Step (a) heating a compound of Formula III

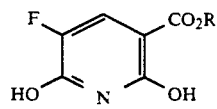

wherein R is lower alkyl or benzyl with POCl₃ in the presence of a lithium reagent and subsequently diluting with a solvent, filtering and distilling to afford the compound of Formula II; and

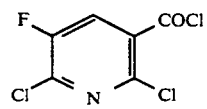

Step (b) reacting the compound of Formula II in water with a base, extracting the resulting solution with a solvent, and neutralizing with an acid to afford the compound of Formula I.

2. A process according to claim 1 wherein the lithium reagent in Step (a) is selected from the group consisting of lithium acetate, lithium carbonate, lithium chloride, lithium hydroxide monohydrate, lithium oxide, lithium phosphate, and lithium sulfate.

3. A process according to claim 2 wherein the lithium reagent is lithium phosphate.

4. A process according to claim 1 wherein in Step (a) the compound of Formula III is heated at about 110° C. to about 250° C. with POCl₃ and a lithium reagent.

5. A process according to claim 4 wherein the compound of Formula III is heated to about 170° C. with POCl₃ and a lithium reagent.

6. A process according to claim 1 wherein in Step (a) the compound of Formula III is heated in an autoclave.

7. A process according to claim 1 wherein in Step (a) 1 mol of the compound of Formula III is heated with about 1 to about 8 lithium salt equivalents.

8. A process according to claim 7 wherein 1 mol of the compound of Formula III is heated with about 5 lithium salt equivalents.

9. A process according to claim 1 wherein the compound of Formula III is selected from the group consisting of: methyl 2,6-dihydroxy-5-fluoronicotinate and ethyl 2,6-dihydroxy-5-fluoronicotinate.

10. A process according to claim 9 wherein the compound of Formula III is methyl 2,6-dihydroxy-5-fluoronicotinate.

11. A process according to claim 1 wherein in Step (b) the base is selected from the group consisting of an alkali metal hydroxide, an alkali metal carbonate, an alkali metal bicarbonate, an alkaline earth metal hydroxide, an alkaline earth metal carbonate, and an alkaline earth metal bicarbonate.

12. A process according to claim 11 wherein in Step (b) the base is an alkali metal hydroxide.

13. A process according to claim 12 wherein the alkali metal hydroxide is sodium hydroxide.

14. A process for the preparation of the compound of Formula II

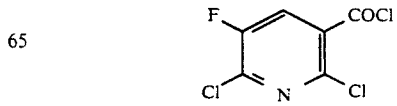

which comprises heating a compound of Formula III

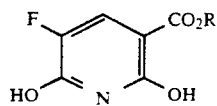

wherein R is lower alkyl or benzyl with POCl₃ in the presence of a lithium reagent and subsequently diluting with a solvent, filtering and distilling to afford the compound of Formula II.

15. A process according to claim 14 wherein the lithium reagent is selected from the group consisting of lithium acetate, lithium carbonate, lithium chloride, lithium hydroxide monohydrate, lithium oxide, lithium phosphate, and lithium sulfate.

16. A process according to claim 15 wherein the lithium reagent is lithium phosphate.

17. A process according to claim 14 wherein the compound of Formula III is heated at about 110° C. to about 250° C. with POCl₃ and a lithium reagent.

18. A process according to claim 17 wherein the compound of Formula III is heated to about 170° C. with POCl₃ and a lithium reagent.

19. A process according to claim 14 wherein the compound of Formula III is heated in an autoclave.

20. A process according to claim 14 wherein 1 mol of the compound of Formula III is heated with about 1 to about 8 lithium salt equivalents.

21. A process according to claim 20 wherein 1 mol of the compound of Formula III is heated with about 5 lithium salt equivalents.

22. A process according to claim 14 wherein the compound of Formula III is selected from the group consisting of: methyl 2,6 dihydroxy-5-fluoronicotinate and ethyl 2,6-dihydroxy-5-fluoronicotinate.

23. A process according to claim 22 wherein the compound of Formula III is methyl 2,6-dihydroxy-5-fluoronicotinate.

24. A process according to claim 1 wherein in Step (a) following filtration the concentrates are treated with an acid chloride before final distillation.

25. A process according to claim 24 wherein the acid chloride is thionyl chloride.

26. A process according to claim 14 wherein following filtration the concentrates are treated with an acid chloride before final distillation.

27. A process according to claim 26 wherein the acid chloride is thionyl chloride.

* * * * *